United States Patent
Bauer et al.

[11] Patent Number: 5,576,012
[45] Date of Patent: Nov. 19, 1996

[54] PHARMACEUTICAL AQUEOUS FORMULATIONS CONTAINING A SPARINGLY SOLUBLE PHARMACEUTICAL ACTIVE COMPOUND WITH A SOLUBILIZING POLYMERIC AGENT

[76] Inventors: Kurt H. Bauer, 4, Im Finkeler, 79112 Freiburg/Br. 33; Markus Kiefer, 6, Unter dem Dorf, 7989 Bad Krozingen, both of Germany

[21] Appl. No.: 66,039

[22] PCT Filed: Oct. 11, 1991

[86] PCT No.: PCT/EP91/01933

§ 371 Date: Aug. 10, 1993

§ 102(e) Date: Aug. 10, 1993

[87] PCT Pub. No.: WO92/10211

PCT Pub. Date: Jun. 25, 1992

[30] Foreign Application Priority Data

Dec. 12, 1990 [DE] Germany ............... 40 39 602.9

[51] Int. Cl.⁶ ................................. A61K 47/32
[52] U.S. Cl. ............ 424/422; 514/772.6; 424/400
[58] Field of Search .................. 424/78.08, 422; 514/772.6; 526/213; 252/DIG. 1

[56] References Cited

U.S. PATENT DOCUMENTS 3,868,447  2/1975  Kliment ........................ 424/81
4,740,546  4/1988  Masuda et al. ............... 524/315

OTHER PUBLICATIONS

Chemical Pharm. Bull, vol. 36, 1988, Okada, et al, pp. 2176–2185.
Acta Pharmaceutica Technologica, vol. 33, No. 1–4, (1987), pp. 136–139.
Hagers Handbuch, 1971, pp. 404–407.
Technologie, Bauer, et al.–1989, pp. 284 and 285.

*Primary Examiner*—Edward J. Webman
*Attorney, Agent, or Firm*—Foley & Lardner

[57] ABSTRACT

The present invention relates to pharmaceutical formulations which comprise at least one pharmaceutical active compound in combination with a polymer of the general formula I or I', in particular for intravenous administration,

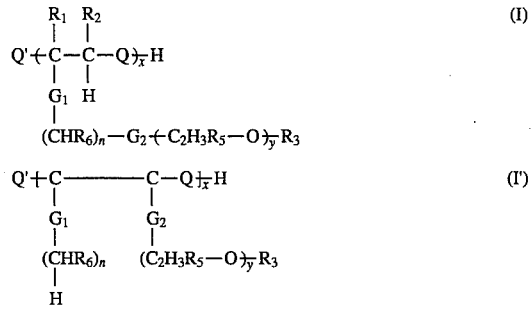

in which $R_1$, $R_2$, $R_5$ and $R_6$ are identical or different and represent hydrogen and a methyl or ethyl group, Q represents a valency, oxygen or an ester or amide bridge and Q' denotes hydrogen if Q represents a valency or oxygen, and is a hydroxyl or amino group if Q represents an ester or amide bridge, x is an integer from 3 to 50, preferably 5 to 40, if Q is a valency or oxygen, and an integer from 3 to 1000, preferably 50 to 100, if Q is an ester or amide function, $G_1$ and $G_2$ are a valency, oxygen or an ester or amide group, it being possible for the two groups to be identical or different, n is an integer from 4 to 44, preferably 12 to 16, y is an integer from 2 to 50, preferably 10 to 40, and $R_3$ is hydrogen or a lower alkyl having 1–6 C atoms.

21 Claims, No Drawings

PHARMACEUTICAL AQUEOUS FORMULATIONS CONTAINING A SPARINGLY SOLUBLE PHARMACEUTICAL ACTIVE COMPOUND WITH A SOLUBILIZING POLYMERIC AGENT

FIELD OF THE INVENTION

The present invention relates to pharmaceutical formulation forms, specifically those which are intended for intravenous use.

DESCRIPTION OF RELATED ART

Pharmaceutical active compounds which are intended for intravasal use must be administered in the form of aqueous solutions. Problems occur here in the case of active compounds which do not have an adequate water-solubility. Thus, for example, the water-solubility of diazepam, nifedipine, propofol and the like is too low to dissolve the therapeutic dose in an acceptable volume. The use of solubilizing auxiliaries is necessary for development of suitable formulations for these active compounds. These auxiliaries must be soluble in water or miscible therewith. They should not have their own pharmacological action and should be distinguished by the lowest possible toxicity. In general, a distinction is made between three groups of solubilizing agents which are used pharmaceutically:

(1) Water-miscible cosolvents
    (propylene glycol, glycerol, ethylene, polyethylene oxides)
(2) Molecular complexes/inclusion compounds
    (Na salicylate, Na benzoate/cyclodextrins)
(3) Amphiphilic substances
    micellar solubilizing agents (surfactants, cosurfactants)
    liposomal solubilizing agents (lecithin)

The water-miscible cosolvents are distinguished by a high dissolving power for lipophilic active compounds. Therapeutically suitable concentrations of the active compounds can be achieved in aqueous solution by addition of a non-stoichiometric amount of these hydrophilic solvents. This form of solubilization is sometimes called hydrotropy. However, the use of these hydrophilic solvents is not acceptable from the toxicological aspect. Thus, in more than 50% of cases, superficial thrombophlebitis has been found. Intravasal hemolytic reactions are detectable for propylene glycol and ethanol. Moreover, injection of these substances is found to be very painful, since tissue lesions occur at the puncture point.

The solubilizing effect of the molecular complexes is as a general rule insufficient for dissolving a therapeutic dose. Since the ligands are employed in equimolar portions, they are present in a high concentration. Possible sensorial (color, smell) and/or pharmacological effects of the ligand therefore cannot be excluded. However, the physical stability of the systems may be mentioned as being advantageous.

Cyclodextrins (CDs), which are obtained by enzymatic degradation of starch, are cyclic molecules which are built up from 6, 7 and 8 glucose units. They are called $\alpha$, $\beta$ and $\gamma$-cyclodextrin. They have the ability to form inclusion compounds with numerous active compound molecules. The driving force for inclusion of the substances is, in addition to van der Waals interactions and the formation of H bridges between the guest molecule and OH groups of the glucose units, the gain in entropy of the water molecules displaced from the hollow space. On inclusion in the hollow space, the guest molecule must eject the water molecules present therein and cast off its own hydrate shell. The water molecules are absorbed by the surrounding water, gain degrees of freedom and contribute towards the stability of the complexes by an increase in entropy. The solubilizing action of cyclodextrins is relatively high; in many cases, it is superior to that of nonionic surfactants. The limiting effect is the poor water-solubility of $\beta$-CD itself, which is 1.8%. $\alpha$-CD dissolves in water to the extent of 17.4%, and $\gamma$-CD to the extent of 25.8%. The toxic effects of cyclodextrins are not insignificant. When administered parenterally, $\beta$-CD exhibits a nephrotoxic action. The hemolytic activity of cyclodextrins is in the sequence $\beta > \alpha > \gamma$-CD (Bloois et al, Acta Pharm. Techn. 33, 1987, page 136). Owing to the not insignificant toxicity, oral administration is preferably indicated for cyclodextrin.

A distinction is made between two classes of amphiphilic auxiliaries: on the one hand micellar solubilization by surfactant-containing systems, and on the other hand liposomal solubilization by double layers of lecithin molecules and phospholipid molecules. The solubilization capacity of the surfactant-containing systems is of the same order of magnitude as liposomal solubilization (Y. Okada et al, Chem. Pharm. Bull, 36, 1988, page 2176). However, it is considerably lower than that of cosolvents, so that this type of solubilization can be used only for low-dosed active compounds.

The difficulties of parenteral administration of surfactants or surfactant systems lies in their incompatibility with cell membranes. During in vitro; experiments with erythrocytes and surfactant solutions, concentration-related changes in the ionic permeability of the membrane up to the presence of membrane pores, leading to release of hemoglobin, are observed. Release of hemoglobin from erythrocytes is called hemolysis. An important prerequisite for the hemolytic activity of surfactants is their ability to become embedded in the cell membrane. By the enrichment of the surfactant molecules in the erythrocyte membrane, pores through which hemoglobin can emerge arise as a result of mixed micelle formation with membrane constituents.

Pharmaceutically usable surfactants should show hemolytic properties to only a very minor extent, if at all. For this reason, only a few amphiphilic substances are available for parenteral formulations (Bauer et al, Pharm. Techn., Thieme Verlag 1989).

The following substances can currently be used:
1) Polyoxyethylene/polyoxypropylene block copolymers (Pluronid F 68 R)
2) Ethoxylated castor oil (Cremophor EL R)
3) Polyoxyethylene-660 12-hydroxystearate (Solutol HS 15 R)
4) Mixed micelles of bile acid salt and lecithin The block polymers based on PEO/PPO show no hemolytic activity. However, their solubilizing properties are very low and are thus unsuitable for the preparation of solubilizates. They are used for stabilization of fat emulsions for parenteral feeding (Hagers Handbuch der Pharm. Praxis (Hager's Handbook of Pharmaceutical Practice), Springer Verlag, 1971).

Ethoxylated castor oil is a considerably better solubilizing agent, to which a clear structural formula cannot be assigned. The product is the mixture, which has not been further purified, of all the reaction products obtainable by reaction of castor oil with ethylene oxide. It exhibits virtually no hemolytic activity, but has other side effects which are to be taken seriously. In some cases, allergic reactions of the immediate type (anaphylactic reactions) have been reported after injection of the substance.

Polyoxyethylene 12-hydroxystearate also unfortunately shows anaphylactoid reactions in animal experiments on dogs, but these are weaker than those of ethoxylated castor oil. The solubilizing properties of the substance are good. The admittedly weak hemolytic activity must be mentioned as a further deficiency.

Bile acid/lecithin mixed micelles are mixed systems comprising phospholipids and naturally occurring bile acid salts. They solubilize less readily than the nonionic surfactants, but display no hemolytic activity. The hemolytically active bile acids are as it were inactivated by the mixed micelle formation with phospholipids. The use of mixed micelles is somewhat limited because of their expensive preparation technology. Another problem is the long-term stability of the systems, since lechithin undergoes autoxidation.

The interactions with biological membranes which can lead to hemolysis in the case of erythrocytes is a major problem of use of surfactants for preparations for injection. There is thus a need for amphiphilic substances which are distinguished by a low or even a lack of hemolytic activity and at the same time have good solubilizing properties.

SUMMARY OF THE INVENTION

This object is achieved by the features characterized in the main claim and promoted by the features of the sub-claims.

It has been found that certain polymeric surfactants offer previously undiscovered possibilities for pharmaceutical use. These surfactants have a powerful hemolytic and/or anaphylactic action as monomers, but surprisingly are tolerated well physiologically as polymers having degrees of polymerization of 3 or more, and in particular have no hemolytic activity. They can be used specifically in formulations to be administered intravenously, but can also be used for improved absorption in formulations for oral and rectal use.

DETAILED DESCRIPTION

The present invention accordingly relates to pharmaceutical formulations which comprise at least one pharmaceutical active compound in combination with a polymer of the general formula I

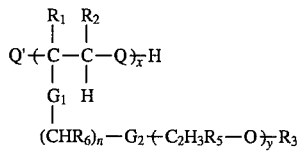

in which $R_1$, $R_2$, $R_5$ and $R_6$ are identical or different and represent hydrogen and a methyl or ethyl group, Q represents a valency, oxygen or an ester or amide bridge and Q' denotes hydrogen if Q represents a valency or oxygen, and is a hydroxyl or amino group if Q represents an ester or amide bridge, x is an integer from 3 to 50, preferably 5 to 40, if Q is a valency or oxygen, and an integer from 3 to 1000, preferably 50 to 100, if Q is an ester or amide function, $G_1$ and $G_2$ are a valency, oxygen or an ester or amide group, it being possible for the two groups to be identical or different, n is an integer from 4 to 44, preferably 12 to 16, y is an integer from 2 to 50, preferably 10 to 40, and $R_3$ is hydrogen or a lower alkyl having 1–6 C atoms. The invention also relates to the preparation of pharmaceutical formulations according to the invention herein described.

These polymers to be used according to the invention in effect comprise 3 parts, that is to say the actual polymer chain (—$CR_1$—$CR_2$—Q), called "A" below, the lipophilic part $(CHR_6)_n$ with the two joining groups $G_1$ and $G_2$, called "B" below, and the hydrophilic end group $(C_2H_3R_5$—$O)_y$, called "E" below.

The structure of the molecular parts A, B and E can be varied within wide limits, but the overall polymer must be water-soluble, pharmaceutically acceptable and stable as an aqueous solution. Since the product is to be injected, it is furthermore necessary that it can be excreted again from the body via the kidneys, that is to say that the molecule is small enough to pass through the kidneys itself, or that it is split by endogenous enzymes into tolerated components which pass through the kidneys.

A is preferably a flexible chain which expediently contains no ring structures. However, ring structures may occur in the side chains, as long as the flexibility of A is not thereby impaired.

The structure of A is not critical and can represent either a polymer, a polycondensate or a polyadduct. A is preferably formed by polymerization of vinyl monomers, in particular acrylic acid, which are correspondingly substituted with the groups B and E. The end groups E are pharmaceutically acceptable, hydrophilic radicals.

A can be an oligomer comprising 3–50, preferably 5 to 40, in particular 10–20 monomer units. Such oligomers are suitable specifically for intravenous administration, since they are excreted directly by the kidney.

However, A can also comprise a large number of monomer units, for example 3–1000, preferably 50–100. Such polymers of high molecular weight are suitable for oral use, or if they contain a group Q which can be split off, can also be injected.

Part B comprises a lipophilic hydrocarbon chain. It can optionally also comprise ring structures, for example phenyl groups. The hydrocarbon chain contains 4–22 C atoms, preferably 12–16 C atoms, in order to ensure adequate lipophilicity.

Part B can be linked to polymer A via various bonding groups $G_1$, which in turn do not impair the lipophilicity of this molecular part. The linkage can thus be effected, for example, via ester, ether, thioether or C—C bonds.

Part E can comprise a large number of hydrophilic structural elements, for example sugar residues or polyethylene glycol radicals. The end group $R_3$ is, for example, a methoxy or ethoxy group. The end group $R_3$ can also comprise a salt structure as a particularly hydrophilic structure, for example an alkali metal salt of an alkylcarboxylic acid or a quaternary alkyl-ammonium group.

Part E can be linked to part B via a multiplicity of bonding groups $G_2$, for example by the groups $G_1$, which are already described above for the linkage of A with B, but also by more hydrophilic structures, such as amide bonds.

Alternatively, groups E and B can also be linked to different C atoms of the polymer part, which results in the tautomeric compounds of the formula I'

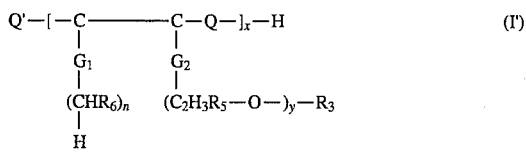

in which all the groups have the above meaning.

Polymer part A can be prepared by conventional polymerization techniques, for example by free radical polymerization of a compound of the formula II

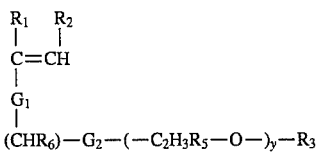
(II)

a polymer of the formula I being formed, or by polymerization of a compound of the formula III

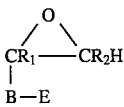
(III)

polymers in which Q represents an ether group being obtained, or by polymerization of compounds IV

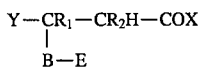
(IV)

in which

X represents an activated group and

Y represents a hydroxyl or amino group, polymers of the formula I in which

Q represents an ester or amide group being obtained. Alternatively, linkages of compounds

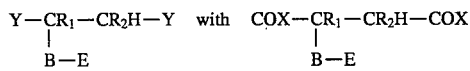

can also be used.

The polymer of the formula I according to the invention can also be achieved by linkage of parts E and/or B and E onto a suitable polymer backbone of the formula A[Z]m, wherein "Z" represents a group which can be replaced in the group $G_1$.

The polymerization can be carried out as free radical polymerization, polycondensation or polyaddition.

Preferred compounds are polymers of the monomer having the formula IIa

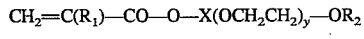
(IIa)

wherein $R_1$ comprises hydrogen or methyl, $R_2$ comprises methyl or ethyl,

X comprises —$(CH_2)_z$—, wherein z can assume integral values from 4 to 22, and y comprises integral values from 2 to 50, and specifically polymers of the formula Ia

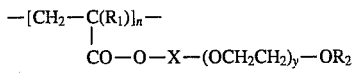
(Ia)

wherein $R_1$, $R_2$, X and y are as defined above and n has a numerical value of 4 or greater than 4, and the average molecular weight of the polymer is less than 15,000 Dalton.

The present invention furthermore relates to the new monomers and polymers, which have particularly suitable use properties in the pharmaceutical formulations according to the invention.

The invention accordingly relates to a compound of the formula IIb

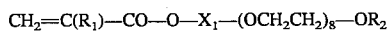
(IIb)

wherein $R_1$ is hydrogen or methyl, $R_2$ is methyl or ethyl and $X_1$ is —$(CH_2)_{10}$—, wherein one or more of the hydrogen atoms independently of one another can be replaced by methyl and/or ethyl.

The preferred abovementioned polymers are prepared by polymerization of a compound of the formula IIa, for example by free radical polymerization. Conventional initiator substances, such as, for example, azodiisobutyrodinitrile (AIBN), are used. The molecular weight and the degree of polymerization can be regulated by using a regulator substance, such as, for example, butanethiol.

The monomers of the formula IIa are prepared by known methods or by methods analogous to known methods or by methods analogous to the methods of the following examples. Thus, for example, compounds of the formula IIa can be prepared by acylation of a corresponding alcohol with acrylyl chloride or methacrylyl chloride.

If the preparation of any particular starting substance is not described in each individual case, this can be prepared by conventional methods or by methods analogous to conventional methods or by methods analogous to those in the following examples. For the preparation, reference is moreover made to DE-A1-36 36 429, EP-A2-02 22 059 and EP-A1-01 57 928, in which similar compounds are described as detergent components and curing agents. The molecular weight and degree of polymerization of the polymers can be determined by conventional methods.

The polymers in general comprise a random mixture of various components which differ in molecular weight and degree of polymerization. Unless expressly mentioned otherwise, the molecular weight and degree of polymerization are determined by laser light scattering (LLS below) in methanol (Blagrove R. J., Revs. Macromol. Chem. C9, 71–90, 1973), vapor pressure osmometry (VPO below) in chloroform (Kamide K., Sawada M., Kobunshi Kagaku [Chem. High Polymers, Japan], 24, 751, 1967) and gel permeation chromatography (GPC below, Moore J. C., Pol. Sci., A2, 835–843, 1964) with polystyrene as the standard and chloroform as the solvent.

The polymers of the formula I are purified by conventional methods and thus brought into a pharmaceutically acceptable purity.

Pharmaceutical formulations can be obtained by processing the polymers of the formula I with pharmaceutical active compounds by conventional methods using known active compounds.

The pharmaceutical active compounds used are substances which are sparingly soluble in water and have a water-solubility of not more than 10 g/liter, or, for example, of not more than 0.1 g/liter.

The active compounds can originate from any field of indication, for example anti-hypertensives, such as nifedipine, anxiolytics and muscle relaxants, such as diazepam, vitamins, such as phytomenadione, or agents for the treatment of hypoprothrombinemia and anesthetics, such as propanidid or propofol.

The solubilization capacity of the polymers according to the invention can be determined with the aid of the so-called shaking method. In this, solutions of different polymer concentrations are thermostatically controlled at 25° C. and periodically shaken with an excess of, for example, diazepam over a period of about 200 hours. The undissolved diazepam is filtered off and the dissolved content is determined by UV spectrometry.

The following results show the outstanding solubilization properties of the polymers according to the invention.

Diazepam without the polymer according to the invention
Water-solubility =0.005%=1.9×10$^{-4}$ mol/liter Diazepam in the presence of the polymer from the following Example 2 (high molecular weight).

a) Representative value:

Polymer concentration: $1.7 \times 10^{-2}$ mol/liter (based on the monomer)

Diazepam concentration: $1.3 \times 10^{-3}$ mol/liter.

b) K value = 0.032 mg of diazepam per mg of polymer (corresponds to the improvement in the solubility of diazepam achieved with each mg of the polymer).

Diazepam in the presence of the polymer from the following Example 3 (low molecular weight).

a) Representative value:

Polymer concentration: $1.7 \times 10^{-2}$ mol/liter (based on the monomer)

Diazepam concentration: $1.1 \times 10^{-3}$ mol/liter.

b) K value = 0.027 mg of diazepam per mg of polymer

For comparison: in the presence of a solution of 0.9 g of polyoxyethylene-660 12-hydroxystearate (Solutol HS 15$^R$, BASF AG) in 100 ml of water, diazepam shows a solubility of $7.8 \times 10^{-4}$ mol/liter and a K value of 0.0178 mg of diazepam per mg of Solutol.

S.Y.O. Lin et al. (Acta Pharm. Technol. (1987), 33, 222) determined a K value of 0.0013 mg of diazepam per mg of Pluronic F 68$^R$ (polyoxyethylene/polyoxypropylene block copolymer).

The invention can be used for improving the bioavailability of water-soluble active compounds.

The amount of polymer according to the invention required depends on various factors, such as the nature of the active compound, its solubility, its effective dose and the intended mode of administration. The amount can be determined by routine methods.

For intravenous injection, the amount of polymer of the formula I is chosen such that a therapeutic dose of the active compound can be dissolved in a volume of, for example, 1 to 5 ml of liquid auxiliaries.

The amount of active compound and polymer according to the invention can easily be determined by conventional methods, for example by bioavailability studies on animals or humans, in which the blood level of the active compound is determined by standard techniques, such as, for example, radioimmunoassay, and by pharmacological studies on humans and animals which allow determination of the pharmacological effect of the active compound.

The polymers are in general used in concentrations of up 30% by weight, for example 0.01 to 25% by weight of the pharmaceutical formulation.

The outstanding tolerance of the pharmaceutical formulations and of the polymers according to the invention can be determined by standard tests.

The hemolytic activity can be determined, for example, as follows.

Human erythrocytes are obtained as a suspension from 400 ml of stabilized human blood (stabilized by addition of a solution of 4.72 g of citric acid, 14.12 g of trisodium citrate and 17.92 g of glucose monohydrate in 1000 ml of water) by centrifuging several times and washing with an isotonic phosphate buffer of pH 7.4 (Ph. Eur. III). To prepare an isotonic solution, the polymers according to the invention are dissolved in the same buffer solution. A defined volume (0.1 ml) of the erythrocyte suspension, which is adjusted to a particular cell count (for example to 1 to $10 \times 10_9$ cells/ml, determined by counting in a Neubauer counting chamber after fixing with Hayem's reagent, (solution of 0.25 g of $HgCl_2$, 2.5 g of $Na_2SO_4$ and 0.5 g of NaCl in 100 ml of distilled water), is added to the polymer solution. The mixture is incubated at 37° C. for at least one hour.

The hemolytic activity is determined by UV spectroscopic determination of the hemoglobin concentration in the supernatant obtained after centrifugation. A surfactant-free solution is used as the control value. A polyoxyethylene-p-t-octyl-phenol solution (Nonidet P 40 R), which effects complete lysis of the erythrocytes, is used as the reference value.

A 2% strength (w/w) isotonic solution of the polymer from Example 2 (high molecular weight) shows a hemolytic activity of 0.7%, which is insignificant, after an incubation time of 8 hours. The erythrocyte concentration in the reaction solution is $1.8 \times 10^8$ erythrocytes/ml.

A 10 percent strength (w/w) isotonic solution of the polymer from Example 3 (low molecular weight) shows a hemolytic activity of 0.6%, which is insignificant, after an incubation time of 1 hour. The erythrocyte concentration in the reaction solution is $2.6 \times 10^8$ erythrocytes/ml.

The pharmaceutical formulations according to the invention can be adjusted to suit the specific modes of administration, such as, for example, oral, or external, such as cutaneous, and specifically parenteral, for example intravenous administration, for example as an injection solution.

The pharmaceutical formulations comprise suitable known auxiliaries.

Water-based intravenous formulations can be prepared by addition of, for example, citric acid and disodium hydrogen phosphate to adjust the pH and isotonisizing additives, such as, for example, glucose.

The following examples illustrate the invention. The abbreviations used have already been defined on the preceding pages.

EXAMPLE 1

Synthesis of 11,14,17,20,23,26,29,32,35-nonaoxahexa-triacontanyl methacrylate a) 11,14,17,20,23,26,29,32,35-Nonaoxahexa-triacontanyl tetrahydropyranyl ether

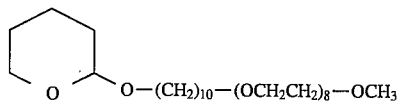

2.7 g (0.12 mol) of sodium are added to a mixture of 46.9 g (0.122 mol) of octaethylene glycol monomethyl ether and 250 ml of toluene and the mixture is heated to about 100° C. As soon as all the Na has disappeared, 34.0 g (0.123 mol) of 10-chlorododecanol tetrahydropyranyl ether are added dropwise at about 70° C. The mixture is allowed to react at 100° C. under a nitrogen atmosphere for several days.

The NaCl which has precipitated is filtered off with suction over a G3 frit and the filtrate is diluted with acetone. The brown precipitate formed by this procedure is centrifuged off. The solvents are removed.

b) 11,14,17,20,23,26,29,32,35-Nonaoxahexa-triacontan-1-ol

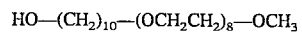

In order to split off the protective group, the residue is diluted with 80 ml (1.37 mol) of analytical grade ethanol and the mixture is heated at a temperature of 60° C. with 3.0 g (0.012 mol) of PPTS (p-pyridinium toluenesulfonate) for 3 hours. It is then diluted with 300 ml of ether, the PPTS which has precipitated is filtered off with suction and the solvents are removed. The liquid product is obtained by flash distillation in vacuo (boiling point 220° C., 8×10$^{-3}$ HPa).

c) 11,14,17,20,23,26,29,32,35-Nonaoxahexa-triacontanyl methacrylate $$CH_2=C(CH_3)-CO-O-(CH_2)_{10}-(OCH_2CH_2)_8-OCH_3$$

1.87 g (0.018 mol) of methacrylyl chloride and a small amount of di-t-butylhydroxytoluene in methylene chloride are added to a solution of 8 g (0.0148 mol) of 11,14,17,20,23,26,29,32,35-Nonaoxahexatriacontan-1-ol and 1.82 g (0.018 mol) of triethylamine in 40 ml of methylene chloride at a temperature of −20° C. The mixture is stirred at room temperature for 12 hours, without cooling. The solvent is removed at room temperature and the crude product is worked up by flash chromatography over silica gel 60 (0.040-0.063 mm) using acetone/ether 50:50. The mobile phase is distilled off at room temperature and the product is obtained as a colorless liquid. $^1$HNMR: 1.2–1.8 ppm (m, 16H, (—CH$_2$)$_8$—), 1.9 ppm (s, 1H, HO—), 3.4 ppm (s, 3H, —OCH$_3$), 3.7 ppm (m, 34H, —(OCH$_2$CH$_2$)$_8$—O—),—(CH$_2$)$_8$—CH$_2$—O—), 4.2 ppm (m, 2H, —COO—CH$_2$—CH$_2$—), 5.5 ppm (s, 1H, H—CH=C(CH$_3$)—COO—), 6.1 ppm (s, 1H, H—CH=C(CH$_3$)—COO—). IR (film): 1700 cm$^{-1}$ (C=O), 1620 cm$^{-1}$ (C=C), 1110 cm$^{-1}$ (C—O).

EXAMPLE 2

Polymer of high degree of polymerization

A solution of 4.1 g (0.0067 mol) of monomer and 0.011 g (0.000067 mol) of AIBN (azoisobutyronitrile) in 10 ml of absolute tetrahydrofuran is frozen with liquid N$_2$. The solution is rendered O$_2$-free by repeated degassing in vacuo and gassing with N$_2$ with subsequent thawing. Polymerization is carried out by heating at 60° C. for 15 hours. Thereafter, the polymer is precipitated in n-hexane three times, dissolved in methylene chloride and dried under a high vacuum for about 30 hours.

$M_w$=380,000 g/mol (determined by LLS); $M_w/M_n$=5.5 (determined by GPC); degree of polymerization $P_w$=620.

EXAMPLE 3

Polymer of low degree of polymerization

The polymerization is carried out under the same conditions as above, using the following batch: 3.6 g (0.006 mol) of monomer, 0.06 g (0.00066 mol) of butanethiol and 0.01 g (0.00006 mol) of AIBN in 8 ml of absolute tetrahydrofuran.

$M_n$ =4300 g/mol (determined by DDO); $M_w/M_n$=1.2 (determined by GPC); degree of polymerization $P_w$=7.

EXAMPLE 4

11,14,17,20,23,26,29-heptaoxatriacontanyl methacrylate is prepared analogously to Example 1 and polymerized analogously to Example 2.

EXAMPLE 5

Pharmaceutical formulations

Injection solutions can be prepared by conventional methods in accordance with the following recipes (amounts stated in grams).

| 1) Propanidid injection solution | |
|---|---|
| Propanidid | 0.500 |
| Polymer from Example 3 | 1.500 |
| Anhydrous citric acid | 0.016 |
| Anhydrous disodium hydrogen phosphate | 0.036 |
| Glucose | 0.355 |
| Water for injection purposes to pH = 6.0. | 10 ml |
| 2) Diazepam injection solution | |
| Diazepam | 0.0100 |
| Polymer from Example 3 | 0.3800 |
| Anhydrous citric acid | 0.0019 |
| Anhydrous disodium hydrogen phosphate | 0.0080 |
| Glucose | 0.0675 |
| Water for injection purposes to pH = 6.9 | 2 ml |
| 3) Phytomenadione injection solution | |
| Phytomenadione (vitamin K3) | 0.0020 |
| Polymer from Example 3 | 0.0600 |
| Anhydrous citric acid | 0.0016 |
| Anhydrous disodium hydrogen phosphate | 0.0036 |
| Glucose | 0.0373 |
| Water for injection purposes to pH = 6.0 | 1 ml |
| 4) Propofol injection solution | |
| Propofol | 0.200 |
| Polymer from Example 3 | 2.300 |
| Anhydrous citric acid | 0.019 |
| Anhydrous disodium hydrogen phosphate | 0.080 |
| Water for injection purposes to pH = 6.9 | 20 ml |

These formulations can be used for the same indications using the same amounts of active compound as the commercially available formulations with the same active compound. Thus, formulation 2 can be administered as an intravenous injection every 4 hours in the treatment of acute anxiety states or muscular spasms.

We claim:

1. A pharmaceutical formulation comprising a pharmaceutically active compound which is sparingly soluble in water and a solubilizing agent, wherein the solubilizing agent is selected from a polymer of the general formula I

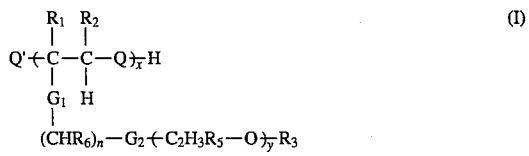

in which $R_1$, $R_2$, $R_5$ and $R_6$ are identical or different and represent hydrogen or a methyl or ethyl group, Q represents a valency, and Q' denotes hydrogen, x is an integer from 3 to 50, G is an ester and $G_2$ is O, n is an integer from 4 to 44, y is an integer from 2 to 50, and $R_3$ is hydrogen or a lower alkyl having 1–6 C atoms, wherein said polymer of formula I is present in an amount of up 30 % by weight of the pharmaceutical formulation.

2. Pharmaceutical formulation according to claim 1, characterized in that the polymer is a polymer of the formula I"

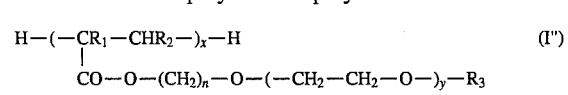

in which $R_1$, $R_2$, $R_3$, x, n and y have the above meaning.

3. Pharmaceutical formulation according to claim 2, characterized in that $R_1$, $R_3$ and x have the above meaning, $R_2$ is hydrogen, n is 10 and y is 8.

4. Pharmaceutical formulation according to claim 3, characterized in that x is 7.

5. Pharmaceutical formulation according to claim 2, characterized in that x is 7.

6. Pharmaceutical formulation according to claim 1 characterized in that x is 7.

7. Pharmaceutical formulation according to claim 1, wherein the polymer is a polymer of the formula I"

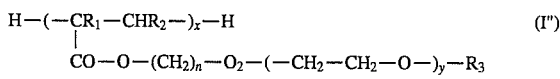

in which $R_1$, $R_2$, $R_5$ and $R_6$ are identical or different and represent hydrogen or a methyl or ethyl group, x is an integer from 3 to 50, n is an integer from 4 to 44, y is an integer from 2 to 50, and $R_3$ is hydrogen or a lower alkyl having 1–6 C atoms.

8. Pharmaceutical formulation according to claim 7, characterized in that $R_1$, $R_3$ and x have the above meaning, $R_2$ is hydrogen, n is 10 and y is 8.

9. Pharmaceutical formulation according to claim 8, characterized in that x is 7.

10. Pharmaceutical formulation according to claim 7 characterized in that x is 7.

11. A pharmaceutical formulation according to claim 7, wherein x is an integer of from 5 to 40.

12. A pharmaceutical formulation as claimed in claim 7, wherein n is an integer of from 12 to 16.

13. A pharmaceutical formulation as claimed in claim 7, wherein y is an integer from 10 to 40.

14. A pharmaceutical formulation as claimed in claim 1, wherein said polymer of formula I is present in an amount of 0.01 to 25 % by weight of the pharmaceutical formulation.

15. A pharmaceutical formulation as claimed in claim 1, wherein said formulation is an isotonic solution in water.

16. A pharmaceutical formulation as claim 1, wherein said formulation further comprises citric acid, disodium hydrogen phosphate and isotonisizing additives.

17. A pharmaceutical formulation as claimed in claim 16, wherein said isotonisizing additive is glucose.

18. A pharmaceutical formulation as claimed in claim 1, wherein x is an integer of from 5 to 40.

19. A pharmaceutical formulation as claimed in claim 1, wherein n is an integer from 12 to 16.

20. A pharmaceutical formulation as claimed in claim 1, wherein y is an integer from 10 to 40.

21. A pharmaceutical formulation according to claim 1, wherein said solubilizing agent is a polymer made from 11,14,17,20,23,26,29,32,35-Nonaoxahexa-triacontanyl methacrylate.

* * * * *